(12) United States Patent
Maini

(10) Patent No.: US 11,766,545 B2
(45) Date of Patent: Sep. 26, 2023

(54) DEFLECTABLE ANCHOR BALLOON CATHETER FOR VASCULAR PROCEDURES

(71) Applicant: EAST END MEDICAL LLC, Lewes, DE (US)

(72) Inventor: Brijeshwar S. Maini, West Palm Beach, FL (US)

(73) Assignee: EAST END MEDICAL LLC, Lewes, DE (US)

( * ) Notice: Subject to any disclaimer, the term of this patent is extended or adjusted under 35 U.S.C. 154(b) by 285 days.

(21) Appl. No.: 17/177,610

(22) Filed: Feb. 17, 2021

(65) Prior Publication Data

US 2021/0252260 A1     Aug. 19, 2021

Related U.S. Application Data

(60) Provisional application No. 62/977,993, filed on Feb. 18, 2020.

(51) Int. Cl.
*A61M 25/10*     (2013.01)
*A61B 17/12*     (2006.01)
(Continued)

(52) U.S. Cl.
CPC ......... *A61M 25/10* (2013.01); *A61B 17/1204* (2013.01); *A61B 17/1214* (2013.01);
(Continued)

(58) Field of Classification Search
CPC ........ A61B 17/12045; A61B 17/12109; A61B 17/12136; A61B 17/1214;
(Continued)

(56) References Cited

U.S. PATENT DOCUMENTS 4,696,304 A    9/1987   Chin
4,813,934 A    3/1989   Engelson et al.
(Continued)

FOREIGN PATENT DOCUMENTS

CL    2019001078 A1    11/2019
CL    2020000232 A1    2/2021
(Continued)

OTHER PUBLICATIONS

First Office Action dated May 7, 2021, from Chinese Application No. 201780074077.5, 15 sheets.
(Continued)

*Primary Examiner* — Deanna K Hall
(74) *Attorney, Agent, or Firm* — FisherBroyles, LLP; Rachel H. Huffstetler

(57) ABSTRACT

A deflectable multidirectional balloon tipped catheter system for conducting peripheral vascular procedures in a remote entry point such as an opposite extremity or other branch point in the arterial system is provided. The catheter system includes a multidirectional catheter body, which includes a wire lumen and a balloon lumen with a control port for connecting to a balloon control and a balloon inflation port, and a compliant or non-compliant anchor balloon connected near the flexible catheter distal end. A method for treating peripheral vascular disease, administration of pharmaceutical and chemotherapeutic agents to the local vascular system, and therapeutic embolization of vascular territories by using the catheter system is provided.

9 Claims, 9 Drawing Sheets

(51) Int. Cl.
  *A61M 25/00* (2006.01)
  *A61M 25/04* (2006.01)
  *A61M 25/09* (2006.01)
(52) U.S. Cl.
  CPC ... *A61B 17/12136* (2013.01); *A61M 25/0026* (2013.01); *A61M 25/0054* (2013.01); *A61M 25/04* (2013.01); *A61M 25/09* (2013.01); *A61M 2025/105* (2013.01); *A61M 2025/1052* (2013.01)
(58) Field of Classification Search
  CPC .. A61B 2017/1205; A61B 2017/22054; A61B 2017/22069; A61M 2025/1052; A61M 25/0026; A61M 25/0054; A61M 25/09; A61M 25/10; A61M 25/104; A61M 2025/1065
  See application file for complete search history.

(56) References Cited

U.S. PATENT DOCUMENTS

| | | | |
|---|---|---|---|
| 5,135,001 | A | 8/1992 | Sinofsky et al. |
| 5,699,805 | A | 12/1997 | Seward et al. |
| 5,792,118 | A | 8/1998 | Kurth et al. |
| 5,865,801 | A | 2/1999 | Houser |
| 6,017,323 | A | 1/2000 | Chee |
| 6,102,926 | A | 8/2000 | Targalia et al. |
| 6,129,672 | A | 10/2000 | Seward et al. |
| 6,440,097 | B1 | 8/2002 | Kupiecki |
| 6,540,712 | B1 | 4/2003 | Parodi et al. |
| 7,666,203 | B2 | 2/2010 | Chanduszko et al. |
| 7,678,081 | B2 | 3/2010 | Whiting et al. |
| 8,096,959 | B2 | 1/2012 | Stewart et al. |
| 8,900,214 | B2 | 12/2014 | Nance et al. |
| 9,072,872 | B2 | 7/2015 | Asleson et al. |
| 9,510,904 | B2 | 12/2016 | Krishnan |
| 9,545,265 | B2 | 1/2017 | Maisano et al. |
| 9,700,351 | B2 | 7/2017 | Maisano et al. |
| 9,757,137 | B2 | 9/2017 | Krolik et al. |
| 2003/0019546 | A1 | 1/2003 | Kanekiyo et al. |
| 2003/0023204 | A1 | 1/2003 | Vo et al. |
| 2003/0229386 | A1 | 12/2003 | Rosenman et al. |
| 2005/0065419 | A1 | 3/2005 | Partridge et al. |
| 2005/0159738 | A1 | 7/2005 | Visram et al. |
| 2005/0197530 | A1 | 9/2005 | Wallace |
| 2005/0245822 | A1 | 11/2005 | Dala-Krishna et al. |
| 2006/0009715 | A1 | 1/2006 | Khairkhahan et al. |
| 2007/0149995 | A1 | 6/2007 | Quinn et al. |
| 2007/0270751 | A1 | 11/2007 | Stangenes et al. |
| 2007/0293724 | A1 | 12/2007 | Saadat et al. |
| 2008/0132937 | A1 | 6/2008 | Hartley |
| 2009/0076498 | A1 | 3/2009 | Saadat et al. |
| 2009/0259272 | A1 | 10/2009 | Reddy et al. |
| 2010/0010488 | A1 | 1/2010 | Kassab |
| 2010/0168777 | A1 | 7/2010 | Stangenes et al. |
| 2010/0286718 | A1 | 11/2010 | Kassab |
| 2011/0270239 | A1 | 11/2011 | Werneth |
| 2012/0203169 | A1 | 8/2012 | Tegg |
| 2012/0259263 | A1 | 10/2012 | Celermajer |
| 2014/0039494 | A1 | 2/2014 | Kick et al. |
| 2014/0081301 | A1 | 3/2014 | Tran |
| 2014/0171903 | A1 | 6/2014 | Roman et al. |
| 2014/0276027 | A1 | 9/2014 | Gaddis |
| 2014/0309675 | A1 | 10/2014 | Maisano et al. |
| 2015/0173794 | A1 | 6/2015 | Kurth et al. |
| 2015/0216620 | A1 | 8/2015 | Davies et al. |
| 2015/0224240 | A1 | 8/2015 | Farnan et al. |
| 2015/0258270 | A1 | 9/2015 | Kunis |
| 2016/0051321 | A1 | 2/2016 | Saiahieh et al. |
| 2016/0081704 | A1 | 3/2016 | Jeon et al. |
| 2016/0100860 | A1 | 4/2016 | Lenker et al. |
| 2016/0143522 | A1 | 5/2016 | Ransbury et al. |
| 2016/0193449 | A1 | 7/2016 | Sarabia et al. |
| 2016/0279393 | A1 | 9/2016 | Anderson et al. |
| 2017/0135559 | A1 | 5/2017 | Horrisberger et al. |
| 2018/0264231 | A1 | 9/2018 | Scheibe |
| 2019/0000544 | A1 | 1/2019 | Govari et al. |
| 2019/0029722 | A1 | 1/2019 | Maini |
| 2019/0134412 | A1 | 5/2019 | Shuros et al. |
| 2019/0209177 | A1 | 7/2019 | Whitfield |

FOREIGN PATENT DOCUMENTS

| | | |
|---|---|---|
| CN | 1599579 A | 3/2005 |
| CN | 103429179 A | 12/2013 |
| CN | 107530532 A | 1/2018 |
| EP | 2233169 A1 | 9/2010 |
| JP | H08117232 A | 5/1996 |
| JP | 2013226429 A | 11/2013 |
| WO | 02/096264 A2 | 12/2002 |
| WO | 2014036317 A2 | 3/2014 |
| WO | 2015058007 A1 | 4/2015 |
| WO | 2018033401 A1 | 2/2018 |
| WO | 2019023609 A1 | 1/2019 |
| WO | 2019113043 A1 | 6/2019 |

OTHER PUBLICATIONS

Written Opinion dated Jun. 16, 2021, from Chilean Patent Application No. 202000403, 16 sheets.
International Search Report and Written Opinion dated May 25, 2021, from International Patent Application No. PCT/US2021/017528, 15 sheets.
Final Office Action dated Aug. 18, 2021, from U.S. Appl. No. 15/784,792, 55 sheets.
Communication Pursuant to Article 94(3) EPC dated Aug. 25, 2021, from EP Application No. 18755361.5, 4 sheets.
Office Action dated Sep. 3, 2021, from Chile Application No. 202000232, 20 sheets.
Notice of Reasons for Rejection dated Sep. 28, 2021, from Japanese Application No. 2019-521811, 4 sheets.
International Search Report and Written Opinion dated Oct. 1, 2021, from PCT Application No. PCT/US2021/018409, 17 sheets.
Final Office Action dated Oct. 7, 2021, from U.S. Appl. No. 16/047,910, 29 sheets.
Office Action dated Oct. 6, 2021, U.S. Appl. No. 16/048,005, 81 sheets.
International Search Report and Written Opinion for International Application No. PCT/US2018/044143 dated Dec. 5, 2018, 16 sheets.
International Search Report and Written Opinion for International Application No. PCT/US2018/044207 dated Oct. 31, 2018, 17 sheets.
International Search Report and Written Opinion for International Application No. PCT/US2020/023518 dated Jun. 23, 2020, 15 sheets.
The extended European search report dated May 12, 2020, from EP Application No. 17862286.6, 8 sheets.
International Search Report and Written Opinion dated Dec. 14, 2017, from PCT/US2017/056843, 10 sheets.
Non-Final Office Action dated Feb. 6, 2020, from U.S. Appl. No. 15/784,792, 29 sheets.
Final Office Action dated Aug. 4, 2020, from U.S. Appl. No. 15/784,792, 38 sheets.
International Search Report and Written Opinion for International Application No. PCT/US2020/036965 dated Sep. 16, 2020, 16 sheets.
International Search Report and Written Opinion for International Application No. PCT/US2020/051228 dated Dec. 1, 2020, 14 sheets.
Non-Final Office Action dated Jan. 26, 2021, from U.S. Appl. No. 15/784,792, 41 sheets.
International Search Report and Written Opinion dated Jan. 13, 2021, from PCT/US2020/53902, 12 sheets.
Non-Final Office Action dated Apr. 30, 2021, from U.S. Appl. No. 16/047,910, 46 sheets.

(56) References Cited

OTHER PUBLICATIONS

Invitation to Respond to Written Opinion from Singapore Patent Application No. 11202000666S, dated Mar. 2, 2021, 11 sheets.
Invitation to Respond to Written Opinion from Singapore Patent Application No. 11202000667S, dated Mar. 2, 2021, 11 sheets.

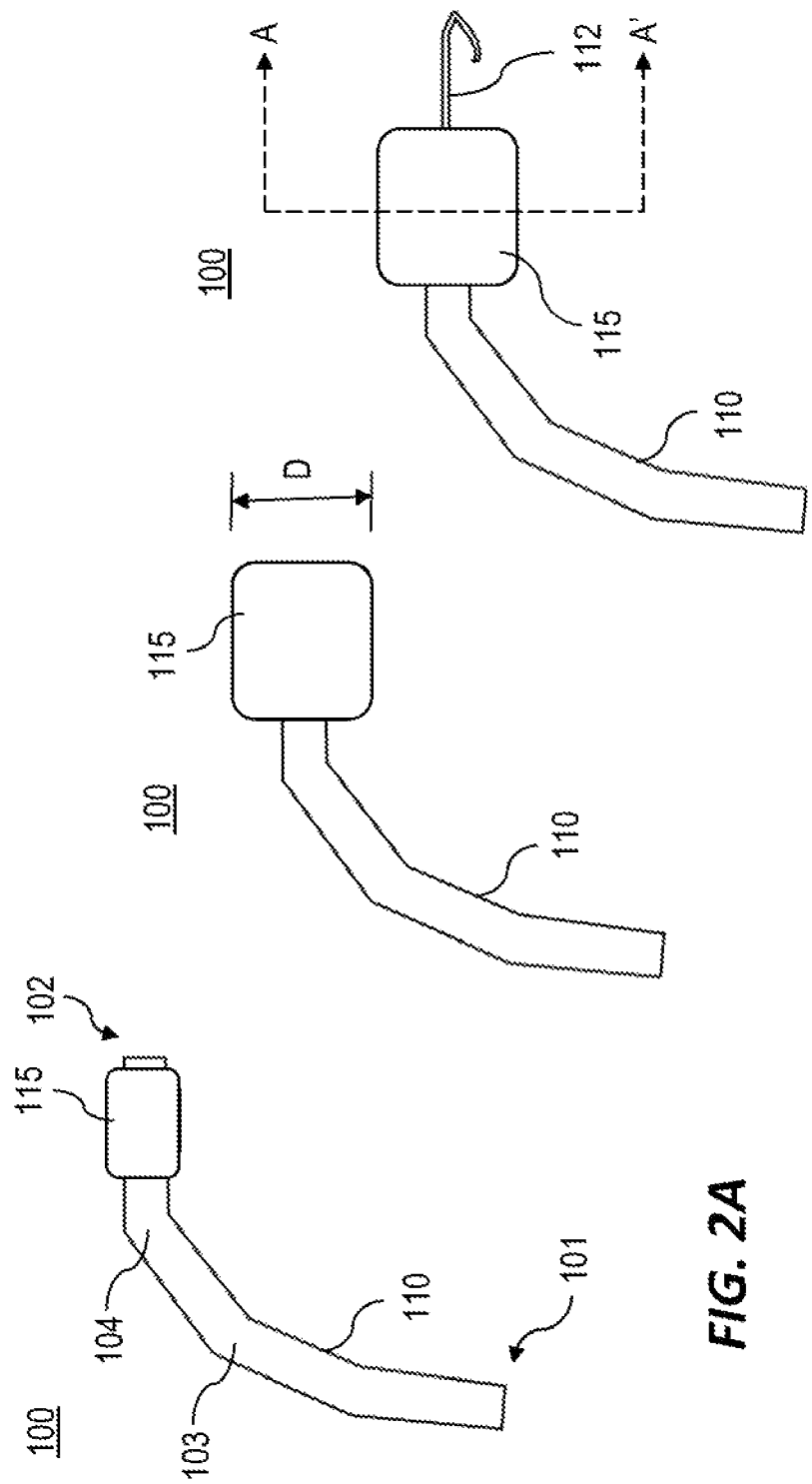

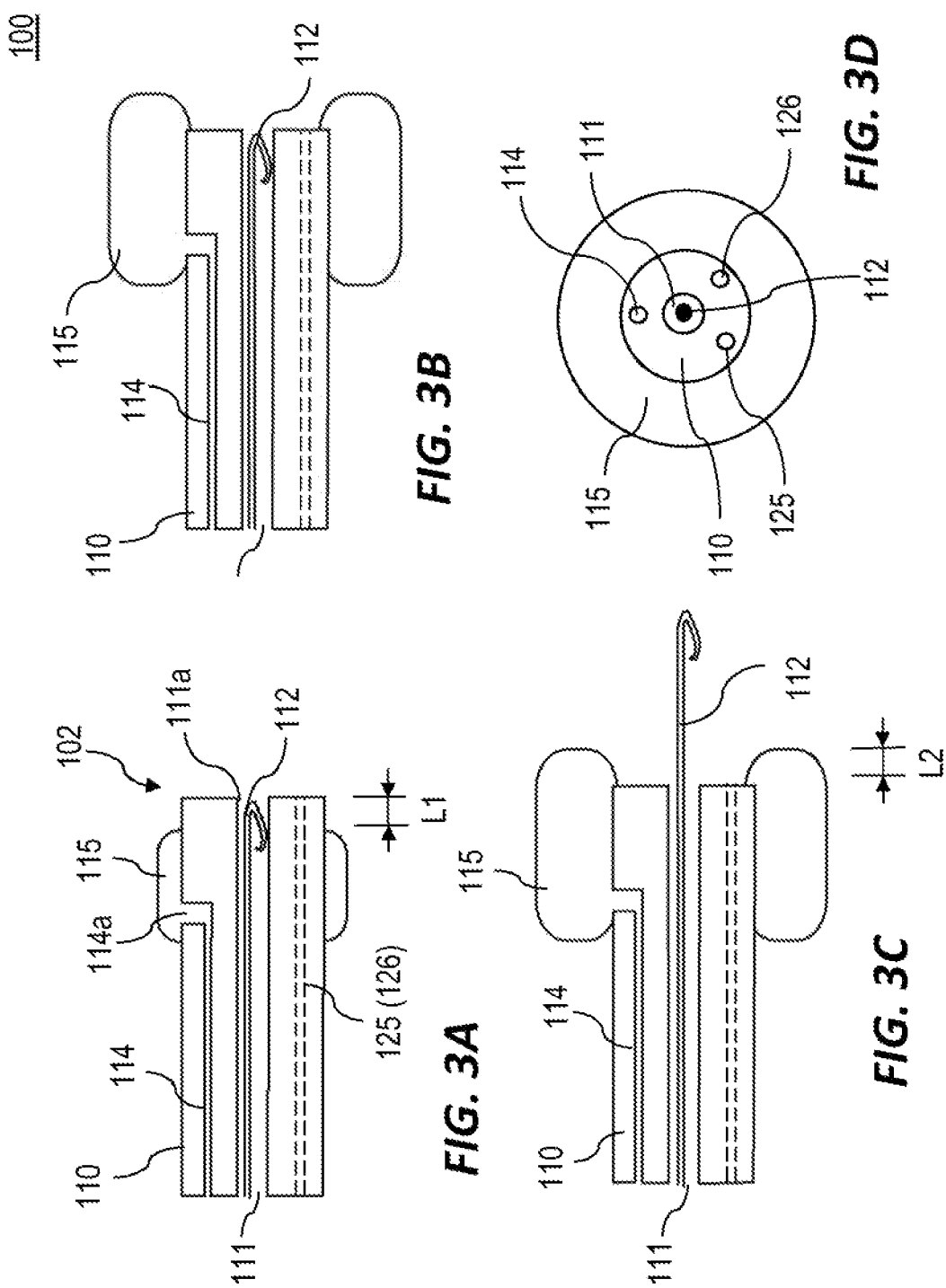

DEFLECTABLE ANCHOR BALLOON CATHETER FOR VASCULAR PROCEDURES

CROSS REFERENCE TO RELATED APPLICATIONS

This application claims the priority of U.S. Provisional Application Ser. No. 62/977,993, filed on Feb. 18, 2020, which is hereby incorporated herein by reference in its entirety.

FIELD OF THE INVENTION

The present invention relates to catheters and catheter based procedures. More particularly, the present invention relates to catheters and procedures for percutaneous interventions, local vascular drug delivery and vascular embolization procedures to treat peripheral vascular disease (PVD), peripheral artery disease (PAD), and deep venous thrombosis (MM.

BACKGROUND

In medicine, peripheral artery occlusive disease, also known as peripheral vascular disease (PVD) and peripheral artery disease (PAD), refers to diseases caused by the obstruction of large peripheral arteries, which can result from atherosclerosis, inflammatory processes leading to stenosis, an embolism or thrombus formation. It causes either acute or chronic ischemia.

Mild PAD may be asymptomatic or cause intermittent claudication; severe PAD may cause rest pain with skin atrophy, hair loss, cyanosis, ischemic ulcers, and gangrene. Diagnosis is by history, physical examination, and measurement of the ankle-brachial index. Severe PAD usually requires angioplasty or surgical bypass and may require amputation. Prognosis is generally good with treatment, although mortality rate is relatively high.

Typically, PAD causes intermittent claudication, which is a painful, aching, cramping, uncomfortable, or tired feeling in the legs that occurs during walking and is relieved by rest. Claudication usually occurs in the calves but can occur in the feet, thighs, hips, buttocks, or, rarely, arms. Claudication is a manifestation of exercise-induced reversible ischemia, similar to angina pectoris. As PAD progresses, the distance that can be walked without symptoms may decrease, and patients with severe PAD may experience pain during rest, reflecting irreversible ischemia. Rest pain is usually worse distally, is aggravated by leg elevation (often causing pain at night), and lessens when the leg is below heart level. The pain may feel like burning, although this finding is nonspecific. About 20% of patients with PAD are asymptomatic, sometimes because they are not active enough to trigger leg ischemia. Some patients have atypical symptoms (e.g., nonspecific exercise intolerance, hip or other joint pain).

As ischemia worsens, ulcers may appear (typically on the toes or heel, occasionally on the leg or foot), especially after local trauma. The ulcers tend to be surrounded by black, necrotic tissue (dry gangrene). They are usually painful, but people with peripheral neuropathy due to diabetes or alcoholism may not feel them. Infection of ischemic ulcers (wet gangrene) occurs readily, producing rapidly progressive cellulitis.

The level of arterial occlusion influences location of symptoms. Aortoiliac PAD may cause buttock, thigh, or calf claudication; hip pain; and, in men, erectile dysfunction. In femoropopliteal PAD, claudication typically occurs in the calf; pulses below the femoral artery are weak or absent. In PAD of more distal arteries, femoropopliteal pulses may be present, but foot pulses are absent.

Dependent on the severity of the disease, a spectrum of treatment options are available. Angioplasty, cryotherapty, or stents (PTA or percutaneous transluminal angioplasty) can be done on lesions in all leg arteries. Plaque excision, in which the plaque is scraped, or undergoes laser removal, off of the inside of the vessel wall. Occasionally, bypass grafting is needed to circumvent a seriously stenosed area of the arterial vasculature. Generally, the saphenous vein is used, although artificial material is often used for large tracts when the veins are of lesser quality. When gangrene of toes has set in, amputation is often a last resort to stop infected dying tissues from causing septicemia. Arterial thrombosis or embolism has a dismal prognosis, but is occasionally treated successfully with thromboylsis.

Revascularization (e.g., femoropopliteal bypass grafting) uses synthetic or natural materials (often the saphenous or another vein) to bypass occlusive lesions. Revascularization helps prevent limb amputation and relieve claudication. Amputation is a procedure of last resort, indicated for uncontrolled infection, unrelenting rest pain, and progressive gangrene.

Routing a therapeutic catheter to a damaged artery can be difficult in patients suffering from PAD or other arterial diseases. Entering directly into an affected femoral artery, for instance routing a catheter from directly above the area and working a device straight down the affected femoral artery is quite difficult, requiring great skill on the part of the surgeon and significant time. Moreover, there is a significant risk of further damaging already damaged arteries and complications approach fifty percent (50%). A better method using therapeutic catheters is to enter through a healthy artery that is distant from the damaged arteries to be treated. An alternative method would require entering through the arm and working a catheter downwards through the aorta and into the iliac artery and then into the affected femoral artery. This long route through the aorta can cause a great deal of discomfort for patients, and also entails relatively high complication rates, and frequently the therapeutic catheters are not long enough.

For example, in endovascular procedures to repair damage to a femoral artery damaged by PAD, the most preferred method would be to enter through a healthy femoral artery in the opposite leg from the procedure, advancing the catheter upwards into the iliac artery of the near leg (i.e., the leg not being repaired), make the U-turn through the lower aorta/common iliac artery and into the opposite side iliac artery, and then proceed down into the affected femoral artery for surgery. However, until now several problems can prevent this method from being used. First, therapeutic catheters are not flexible enough to make the bend from the near iliac artery into the opposite iliac artery and down into the femoral artery—referred to as the "U-turn". This bend essentially entails a nearly 180 degree turn—impossible for currently available large-bore catheters. Second, flexible catheters, can make the turn, but they cannot hold themselves in the opposite femoral artery when attempting to route a stiff guide wire through, which stiff guide wire could then be used to guide a therapeutic catheter. As an operator attempts to route a stiff guide wire through the flexible catheter, the flexible catheter displaces out of the femoral and iliac arteries when the stiff wire reaches the U-turn, and moves up into the aorta. At that point the stiff guide wire is not flexible enough to re-route the flexible catheter back into the iliac and femoral arteries. This same difficulty applies in other procedures where a therapeutic catheter must be routed to a location through a tortuous vascular path to support a stiff guide wire for therapeutic catheter routing. Therefore, until now PAD procedures on patients with difficult anatomy requiring entry from an opposite extremity could not be performed reliably, and the patients have been left with the option of no treatment or procedures with greater risks of complications.

To date most attempts at solving the problem have focused on increasing the flexibility of the tips of larger therapeutic catheters and stiff guide wires. This results in more expensive and complicated devices, as well as greater skill on the part of the operator to effectively use the devices. The difficulty of using the devices also increases the time required for a surgeon to complete a procedure, which both increases the costs and increases the potential for complications.

Deep venous thrombosis (DVT) is a condition that occurs when a blood clot forms in a patient's vein deep in the body, usually in the patient's legs or the feet. The clot can block proper blood flow and may lead to severe injury or death if the clot breaks off and travels through the bloodstream to other areas of the body, such as the brain or lungs. Venous thromboembolism (VTE) is the third leading vascular disease after acute myocardial infarction and stroke. VTE, which encompasses deep vein thrombosis DVT and pulmonary embolism (PE), contributes to a yearly economic burden of 7 to 10 billion dollars in the USA.

A thrombus is typically classified as acute if it has formed within 2 to 4 weeks of diagnosis. Duplex ultrasound characteristic of acute DVT include a smooth homogenous thrombus appearance, soft or spongy texture, hypoechogenicity, poor wall attachment or free floating, surrounding dilated vessel size and absence of collaterals with no flow noted in the vein on spectral Doppler. Approximately 25-50% of patients with lower extremity DVT develop post-thrombotic syndrome (PTS), despite anticoagulation therapy. Symptoms of PTS include swelling, pain, heaviness, and venous claudication which can worsen with dependency of the leg. The primary goal of catheter directed interventions for acute DVT is to prevent or reduce the likelihood of developing PTS and VTE. Catheter-directed pharmacologic thrombolysis (CDPT), mechanical and pharmacomechanical thrombectomy, aspiration thrombectomy are being used more commonly to prevent PTS and VTE. The most relevant major complications identified in a pooled analysis of more than 1,000 patients included major hemorrhage (8.3%), symptomatic PE (0.9%), death (0.3%), and intracranial hemorrhage (0.2%).

SUMMARY

Embodiments of the disclosed invention provides a multidirectional balloon tipped catheter system to seek a solution through simplified components and a simple multi-step methodology that has not been used prior.

These advantages and others are achieved, for example, by a multidirectional balloon tipped catheter system for conducting vascular procedures upon arteries in an extremity from an entry point or other branch point opposite to the extremity in the arterial system. The catheter system includes a multidirectional catheter body having a proximal end and a distal end. The multidirectional catheter body includes a plurality of curls and flexion points for multidirectional deflections. The catheter body includes a plurality of lumens which include at least one wire lumen including an exit port at the distal end and at least one balloon lumen including a balloon port near the distal end. The catheter system further includes an anchor balloon mounted to near the distal end of the catheter body and a guide wire placed in the wire lumen. The anchor balloon is in fluid communication with the balloon port and overhangs the distal end of the catheter body by a predetermined distance when the anchor balloon is inflated. The guide wire is configured to protrude beyond the distal end of the catheter body when the guide wire is in use.

The anchor balloon may be inflated with a fluid including air, saline, or contrast, and may be configured to be inflated in various sizes. The anchor balloon may overhang the distal end of the catheter body by two to three millimeters when the anchor balloon is inflated. A diameter of the anchor balloon may be configured to occlude a vascular channel at a selected location. A diameter of the wire lumen may be equal to or greater than 0.91 mm. A distance of a distal end of the anchor balloon from the distal end of the catheter body may be in a range of 10 mm to 20 mm when the anchor balloon is deflated. The catheter body may be configured to be insertable into a femoral artery or other vascular access. The plurality of lumens may further include one or more additional lumens for delivery of pharmaceuticals, chemotherapeutics and embolization products to a selected location.

These advantages and others are achieved, for example, by a method for conducting vascular procedures upon arteries in an extremity from an entry point opposite to the extremity with a multidirectional balloon tipped catheter system. The method includes processes of inserting the multidirectional balloon tipped catheter system into the entry point in a near femoral artery or other vascular access, advancing the catheter system toward a branch point that is connected to the extremity, inflating the anchor balloon at a first size, navigating the catheter system to an ostium of the extremity, inflating the anchor balloon at a second size that is larger than the first size, anchoring the catheter system at the ostial and proximal segment of the extremity by using the anchor balloon inflated at the second size where the extremity is occluded by the anchor balloon, advancing the guide wire into a distal segment of the extremity for diagnostic or therapeutic procedures, and deflating the anchor balloon to free the occlusion in the extremity.

The method may further include inserting an entry sheath into the entry point into which the catheter system is inserted through the entry sheath. The method may further include performing the diagnostic or therapeutic procedures while the catheter system is anchored at the ostial and proximal segment of the extremity. The method may further include further advancing the catheter system into the distal segment of the extremity for further diagnostic or therapeutic procedures. The method may further include administering pharmaceutical and chemotherapeutic agents to local vasculature of the extremity using the catheter system while the anchor balloon is inflated. The method may further include removing the catheter body with deflated anchor balloon while leaving the guide wire in place, and withdrawing the entry sheath over the guide wire while leaving the guide wire in place. The guide wire may be then available to insert a long sheath or therapeutic catheter for therapeutic procedures. The method may further include occluding blood vessels with embolization coils, glues, plugs and other occluder devices using the catheter system while the anchor balloon is inflated.

These advantages and others are achieved, for example, by a multidirectional balloon tipped catheter system for conducting closed loop perfusion and reperfusion for treatment of deep venous thrombosis. The catheter system includes a multidirectional catheter body having a proximal end and a distal end and including a plurality of curls and flexion points for multidirectional deflections. The catheter body includes a plurality of lumens which include a main lumen including an exit port at the distal end and at least one balloon lumen including a balloon port near the distal end. The catheter system further includes an anchor balloon mounted to near the distal end of the catheter body and an inner catheter device disposed in the main lumen. The anchor balloon is in fluid communication with the balloon port and overhangs the distal end of the catheter body by a predetermined distance when the anchor balloon is inflated. The inner catheter device includes a flexible inner catheter body including a center lumen, at least one balloon lumen, and a plurality of additional lumens. The inner catheter body is configured to advance beyond the distal end of the multidirectional catheter body. The additional lumens include exit ports open to outside of the inner catheter body. The inner catheter device further includes an anchor balloon mounted to near the distal end of the inner catheter body. The anchor balloon is in fluid communication with the balloon lumen and overhangs the distal end of the inner catheter body by a predetermined distance when the anchor balloon is inflated.

The anchor balloon and the anchor balloon of the inner catheter device may be inflated with a fluid including air, saline, or contrast, and may be configured to be inflated in various sizes. The exit ports of the additional lumens of the inner catheter device may be formed at proximal side from the anchor balloon of the inner catheter device. The multidirectional catheter body may include channels that are connected to the main lumen and are open to outside of the multidirectional catheter body. The inner catheter body may include channels that are connected to the center lumen and are open to outside of the inner catheter body. The channels of the multidirectional catheter body may be configured to be substantially aligned with the channels of the inner catheter body to form open fluid paths, when the inner catheter device advances by a predetermined distance. The exit ports of the additional lumens of the inner catheter device may be configured to be exposed outside the main lumen for delivery of pharmaceuticals, chemotherapeutics and embolization products to a selected location, when the inner catheter device advances by the predetermined distance.

BRIEF DESCRIPTION OF THE DRAWINGS

The preferred embodiments described herein and illustrated by the drawings hereinafter be to illustrate and not to limit the invention, where like designations denote like elements.

FIGS. 2A-2C show an embodiment of multidirectional balloon tipped catheter system of the disclosed invention for conducting vascular procedures upon arteries in an extremity from an opposite entry point or other branch point in the arterial system.

FIGS. 3A-3C show longitudinal side views of the distal end portion of the multidirectional balloon tipped catheter system.

FIG. 3D shows a transverse cross-sectional view of the section A-A' of the distal end portion of the multidirectional balloon tipped catheter system shown in FIG. 2C.

DETAILED DESCRIPTION

Figure 1A:
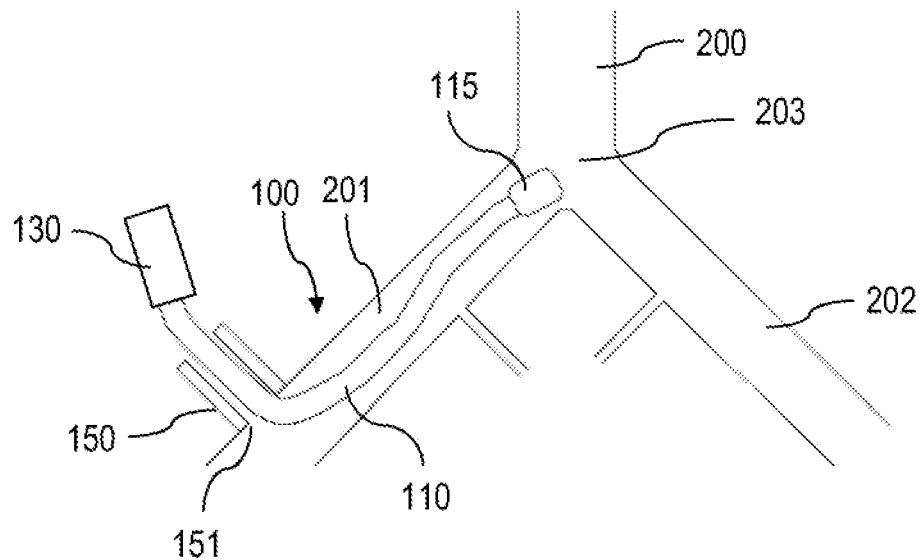
FIGS. 1A-1D show exemplary illustrations which show multidirectional balloon tipped catheter system for conducting vascular procedures upon arteries in an extremity from an opposite entry point or other branch point in the arterial system.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Embodiments of the disclosed invention seek a solution through simplified components and a simple multi-step methodology that has not been used prior. Embodiments include a method and apparatus which will allow an operator performing endovascular procedures, such as on a femoral artery, to anchor a flexible catheter in an upstream location in an artery so that a stiff guide wire can then be routed through the flexible catheter, which stiff guide wire can subsequently be used to route a medium or large catheter or sheath to conduct the actual therapeutic surgery, whether that involves an angioplasty balloon catheter, or inserting a stent, or some other sort of device or surgical procedure.

Currently, none of the procedures for treating PAD through the use of a catheter are able to cross from one extremity to the other through the arteries of a patient with difficult anatomy. Currently available balloon catheters are not useful for this purpose either. In this regard, "difficult anatomy" is the inability to pass a catheter from a proximal entry point to a location in an opposite side artery requiring a therapeutic procedure. This difficulty may be due, for example, to tortuous vessels with marked curvature, narrow iliac bifurcation with angles less than 45 degrees (i.e., a U-turn of nearly 180 degrees for femoral artery procedures), or due to previous endovascular intervention. None of the existing devices and procedures allow introduction into the femoral artery of the near leg of a patient with difficult anatomy, and progression of a therapeutic catheter to the femoral artery of the opposite leg.

Therefore, in order to get a catheter with therapeutic devices to a selected location in an artery for catheter based procedures to treat PAD, in patients with difficult anatomy, an operator must first pass a stiff wire from the near leg to the opposite leg via the common iliac artery and pass the therapeutic catheter over the stiff wire, or alternatively pass a sheath over the stiff wire through which a therapeutic catheter device may be passed.

To date most attempts are being made for local drug delivery for treating malignancies etc. The difficulty in such therapeutics is the vascular site selectiveness such that normal tissue may remain unharmed. Solving the problem have focused on increasing the flexibility of the tips of larger therapeutic catheters and stiff guide wires. This results in more expensive and complicated devices, as well as greater skill on the part of the operator to effectively use the devices. The difficulty of using the devices also increases the time required for an operator to complete a procedure, which both increases the costs and increases the potential for complications.

The problem therefore, is how to get such a stiff guide wire and a catheter which is occlusive such as to deliver pharmaceuticals, chemotherapeutics and embolization products to the selected location. Embodiments provide a solution through a multidirectional balloon tipped catheter that has not been used prior and solves this problem.

With reference to FIGS. 1A-1D, shown are exemplary illustrations which show multidirectional balloon tipped catheter system 100 for conducting vascular procedures upon arteries in an extremity from an opposite entry point or other branch point in the arterial system. For illustration purpose, FIGS. 1A-1D show aorta artery 200 splitting to become paired iliac arteries 201, 202 in which the vascular procedures with the multidirectional balloon tipped catheter system 100 is conducted. As shown in FIG. 1A, the catheter system 100 is inserted in the left iliac artery 201 through an entry sheath 150, and proceeds to the right iliac artery 202 through a branch 203 between the left iliac artery 201 and the right iliac artery 202. When the catheter system 100 passes through the branch 203, it needs to make the U-turn through the branch 203 (lower aorta/common iliac artery) to proceed into the right iliac artery 202, and then to proceed down into the affected femoral artery for surgery. These processes will be described later in detail. Embodiments of the disclosed invention provide multidirectional balloon tipped catheter 100 that enables vascular procedures upon arteries in an extremity from an opposite entry point or other branch point in the arterial system, overcoming the problems discussed above.

With reference to FIGS. 2A-2C shown are an embodiment of multidirectional balloon tipped catheter system 100 of the disclosed invention for conducting vascular procedures upon arteries in an extremity from an opposite entry point or other branch point in the arterial system. With reference to FIGS. 3A-3C shown are longitudinal cross-sectional side views of the distal end portion of the multidirectional balloon tipped catheter system 100. With reference to FIG. 3D, shown is a transverse cross-sectional view of the section A-A' of the distal end portion of the multidirectional balloon tipped catheter system 100 shown in FIG. 2C.

The multidirectional balloon tipped catheter system 100 includes a multidirectional or deflectable flexible catheter body 110 that includes a proximal end 101 and a distal end 102. The catheter body 110 is French sizes, and includes curls and flexion points to be multidirectional or deflectable. For example, the catheter body 110 may include a plurality of flexion points 103, 104 to facilitate the multidirectional deflections or bending. The catheter body 110 has a length sufficient to reach a selected location in a patient's opposite extremity or other branch point in the arterial system. The catheter body 110 is configured to be insertable into a femoral artery or other vascular access as illustrated in FIG. 1A. The catheter body 110 includes a plurality of lumens. The plurality of lumens includes at least one wire lumen 111 including a wire access port (not shown) accessible to an operator at said catheter proximal end 101 and a wire exit port 111a at the flexible catheter distal end 102, and a balloon lumen 114 for inflating and deflating at least one anchor balloon 115. The balloon lumen 114 includes a balloon control port (not shown) for connecting to a balloon control device accessible to an operator at the catheter proximal end 101 and a balloon port 114a connected to the balloon 115 near the multidirectional catheter distal end 102.

The plurality of lumens may include one or more additional lumens for delivery of pharmaceuticals, chemotherapeutics and embolization products to the selected locations or areas. FIG. 3D exemplarily shows two additional lumens 125, 126. However, the number of the additional lumens is not limited to two. The additional lumens 125, 126 may be used for local drug delivery for treating malignancies, for local vascular drug delivery and vascular embolization procedures, and for flushing and aspirating, etc. The additional lumens 125, 126 have access ports at the proximal end 101 of the catheter body 110, and external devices, such as drug delivery devices, may be connected to the access ports of the additional lumens 125, 126.

The multidirectional balloon tipped catheter system 100 includes compliant or non-compliant anchor balloon 115 that is mounted on the multidirectional catheter body 110 near the distal end 102 of the catheter body 110. FIGS. 2A and 2B show deflated anchor balloon 115, and FIGS. 2B and 3B show inflated anchor balloon 115 at the distal end 102 portion of catheter body 110. The anchor balloon 115 is connected to the balloon port 114a of the catheter lumen 114, and is in fluid communication through the balloon lumen 114. Fluid, which is injected or removed at the balloon control port at the proximal end 101, inflates or deflates the anchor balloon 115 through the balloon lumen 114.

The anchor balloon 115 may be inflated with air, saline, contrast and other solutions, and may be inflated to various sizes. The anchor balloon 115 is placed at a selected distance from the distal end 102 of the catheter body 110. For example, when the anchor balloon 115 is deflated, the distance L1 of a distal end of the anchor balloon 115 from a distal end 102 of the catheter body 110 may be in the range 10 mm (0.4 inches) to 20 mm (0.8 inches). When the anchor balloon 115 is inflated, the anchor balloon 115 may overhang the distal end 102 of the catheter body 110 by a distance L2 which may be two to three millimeters.

The multidirectional balloon tipped catheter system 100 includes stiff guide wire 112 disposed in the wire lumen 111. The catheter body 110 includes pacing lead lumen 111 that includes a cord access port (not shown) accessible to an operating device at the proximal end 101 and exit port 111a at the distal end 102 of the catheter body 110. The wire lumen 111 may be positioned at a center of the cross-section of the catheter 110 as shown in FIG. 3D. The diameter of the pacing lead lumen 111 may be equal to or greater than 0.91 mm (0.035 inches). The guide wire 112 may be placed inside the wire lumen 111 while the catheter system 100 advances toward a proper position.

The diameter D of the anchor balloon 115, when fully inflated, is such as to occlude the artery or the vascular channel at the selected location, thereby the inflated anchor balloon 115 stabilizes the catheter system 100 to allow the stiff guide wire 112 to pass through the distal end 102 of the catheter body 110. When the catheter system 100 is stabilized, the guide wire 112 may advance out of the wire lumen 111 beyond the distal end 102 of the catheter body 110 to perform diagnostic or therapeutic procedures. FIGS. 2C and 3C show the guide wire 112 advancing out of the distal end 102 of the catheter body 110.

Figure 4:
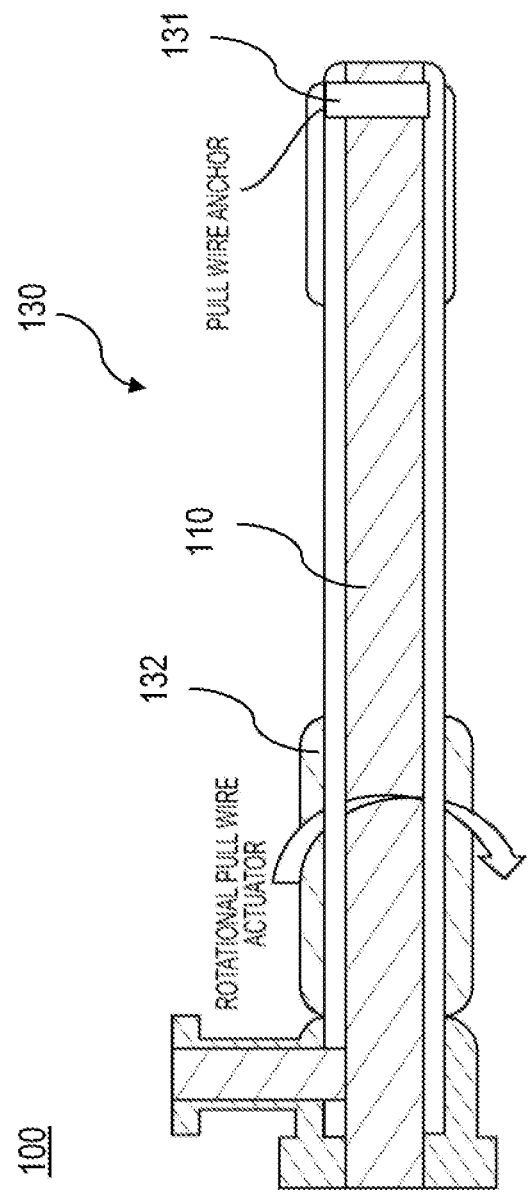
FIG. 4 shows an exemplary embodiment of a mechanical deflection mechanism that can be employed at the proximal end portion of the catheter body to control deflections of the catheter system.

With reference now to FIG. 4, shown is an exemplary embodiment of a mechanical deflection mechanism 130 that can be employed at the proximal end 101 portion of the catheter body 110 to control deflections of the distal end portion of the catheter system 100. Mechanical deflection mechanism may enable distal end of catheter body 110 to be deflected or angulated to various angles with respect to a longitudinal axis (from the proximal end 101 to the distal end 102) of the catheter system 100. Mechanical deflection mechanism or device 130 may include a pull wire anchor 131 affixed to the catheter body 110 and pull wire actuator 132 connected to pull wire anchor 131 with pull wire (not shown). Rotation of pull wire actuator 132, as shown, may exert force on pull wire anchor 131 that deflects or angulates distal end of the catheter body 110. Pull wire actuator 132 may be rotated by handle connected thereto (not shown). The deflection mechanism 130 together with the flexion points and curls formed in the catheter body 110 enables the distal end of the catheter body 110 to deflect at a stiff angle such as more than 135 degrees to make the U-turn through the branch 203 to proceed, for example, into the right iliac artery 202 from the left iliac artery 201. U.S. patent application Ser. No. 17/061,761 filed on Oct. 2, 2020 by the same inventor discloses an improved handle that can be employed in the catheter system of the disclosed invention to provide deflections.

Figure 1B:
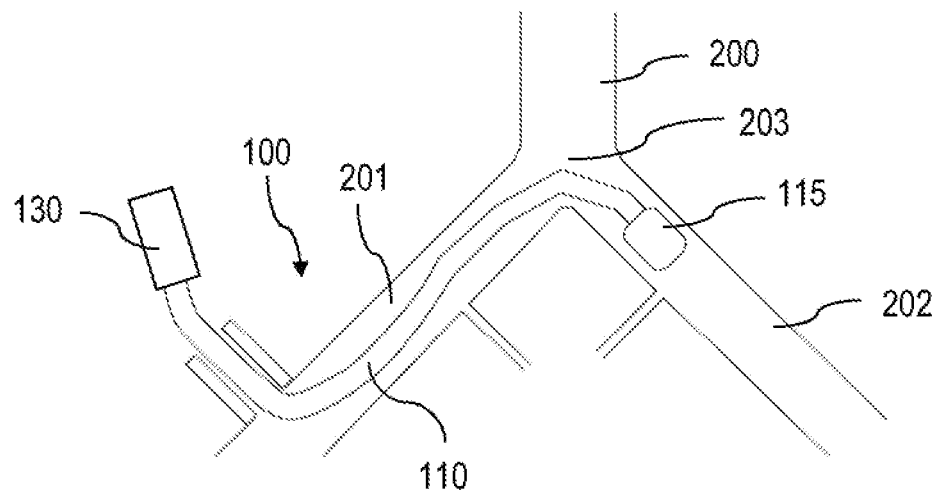
Figure 1C:
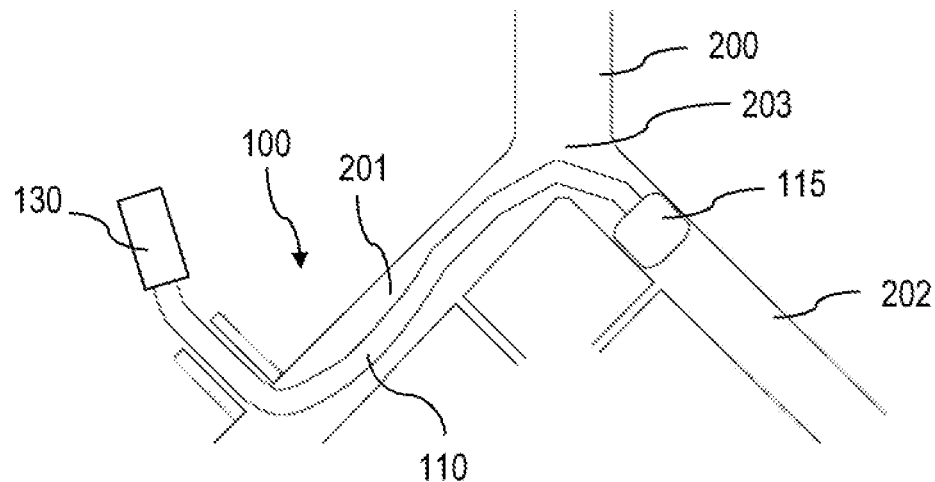
Figure 1D:
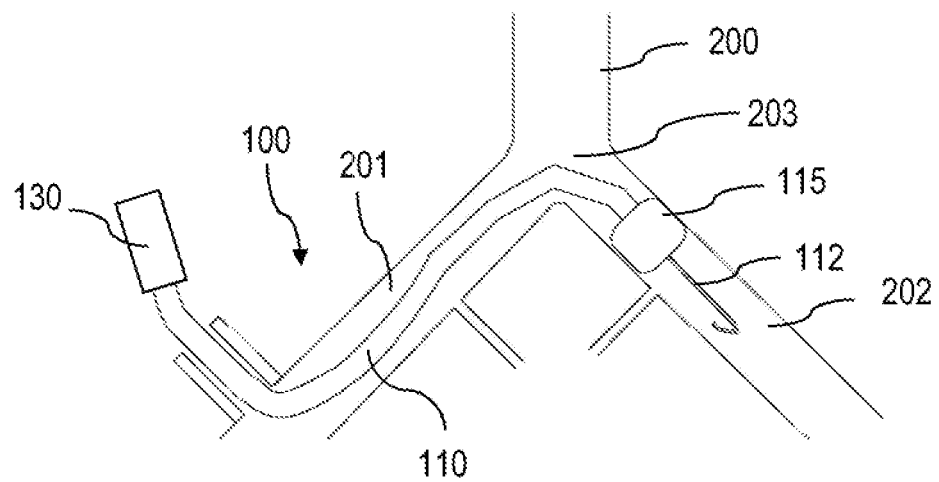
Figure 5:
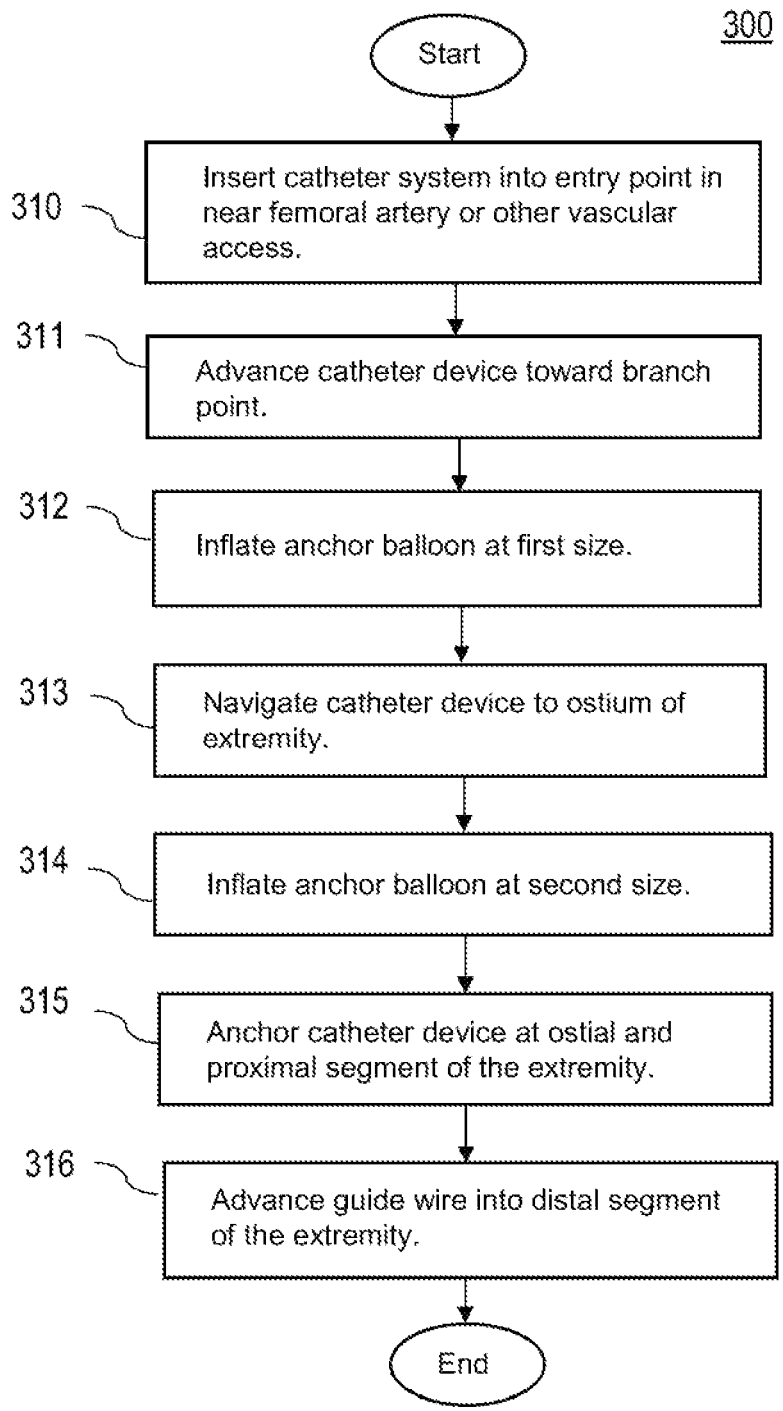
FIG. 5 shows a workflow diagram for a method for conducting vascular procedures upon arteries in an extremity from an entry point opposite to the extremity using a multidirectional balloon tipped catheter system.

With reference to FIG. 5, shown is a workflow diagram for a method 300 for conducting vascular procedures upon arteries in an extremity from an entry point opposite to the extremity using a multidirectional balloon tipped catheter system 100 including a multidirectional catheter body 110. The catheter system 100 is inserted into the entry point 151 in a near femoral artery or other vascular access, block 310. In the exemplary illustrations shown in FIGS. 1A-1D, the catheter system 100 is inserted through the entry point 151 at left iliac/femoral artery 201 which is located opposite to the extremity (right iliac/femoral artery 202). The catheter system 100 is advanced toward branch point 203 that is connected to the extremity (right iliac/femoral artery 202), block 311. The anchor balloon 115 is inflated at a first size, block 312, while the catheter system 100 navigates toward the branch point 203. The catheter system 100 is navigated to an ostium of the extremity 202, block 313, as shown in FIG. 1B. The anchor balloon 115 is inflated at a second size that is larger than the first size, block 314. The distal end 102 of the catheter system 100 is anchored at the ostial and proximal segment of the extremity 202 by using the anchor balloon 115 inflated at the second size. The extremity 202 may be occluded by the anchor balloon 115 inflated at the second size, block 315, as shown in FIG. 1C. The guide wire 112 is advanced into a distal segment of the extremity 202 for diagnostic or therapeutic procedures, block 316, as shown in FIG. 1D. Then, the anchor balloon 115 may be deflated to free the occlusion in the extremity 202.

In order to insert the catheter system 100 into the entry point 151 in a near femoral artery or other vascular access, a short entry sheath 150 may be inserted into the entry point 151. The catheter system 100 is inserted into the entry point 151 through the entry sheath 150. Diagnostic or therapeutic procedures may be performed while the catheter system 100 is anchored at the ostial and proximal segment of the extremity 202. The catheter system 100 may be further advanced into the distal segment of the extremity 202 for further diagnostic or therapeutic procedures. While the anchor balloon 115 is inflated and the catheter system 100 is anchored, pharmaceutical and chemotherapeutic agents may be administered to local vasculature of the extremity 202 using the catheter system 100.

The catheter body 110 with deflated anchor balloon 115 may be removed while leaving the guide wire 112 in place. The entry sheath 150 over the guide wire 112 may be withdrawn while leaving the guide wire 112 in place. In this stage, the guide wire 112 is then available for inserting a long sheath or therapeutic catheter for therapeutic procedures. The guide wire 112 may guide the long sheath or therapeutic catheter into a selected point in the extremity 202. The blood vessels in the extremity 202 may be occluded with embolization coils, glues, plugs and other occluder devices using the catheter system while the anchor balloon is inflated.

Figure 6A:
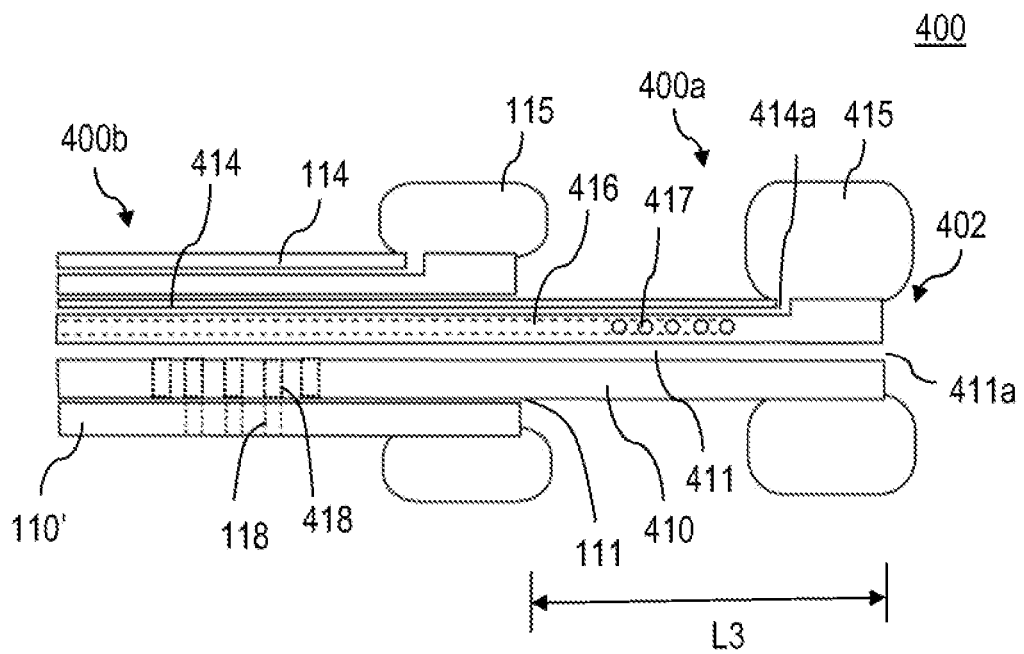
FIG. 6A shows a longitudinal cross-sectional side view of a distal end portion of another embodiment of the multidirectional balloon tipped catheter system.
Figure 6B:
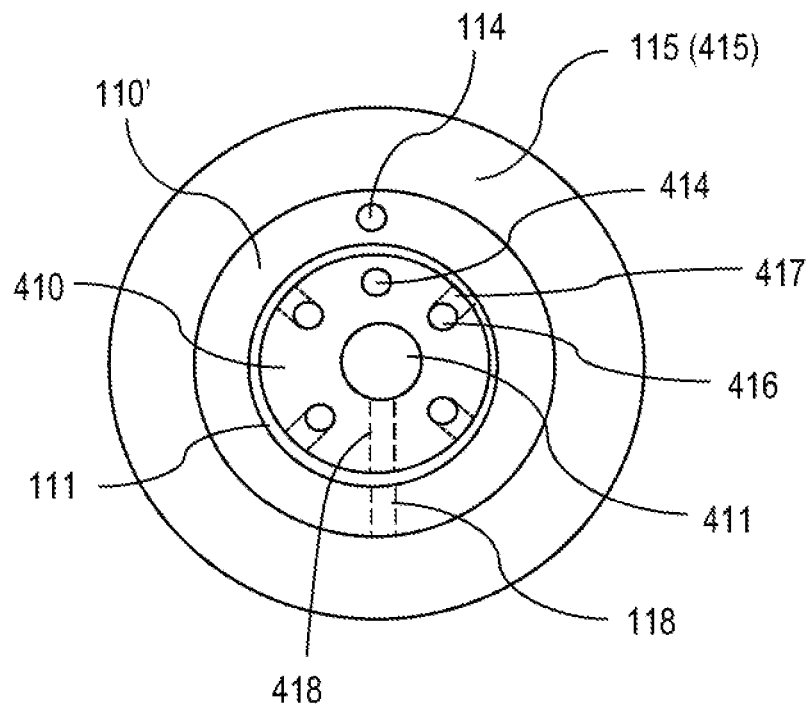
FIG. 6B shows a transverse cross-sectional view of the distal end portion of the multidirectional balloon tipped catheter system.

With reference to FIG. 6A, shown is a longitudinal cross-sectional side view of a distal end portion of another embodiment of the multidirectional balloon tipped catheter system 400. With reference to FIG. 6B, shown is a transverse cross-sectional view of the distal end portion of the multidirectional balloon tipped catheter system 400. The catheter system 400 has a similar structure to the catheter system 100 shown in FIGS. 2A-3D, except that the guide wire 112 of the catheter system 100 is replaced with an inner catheter system 400a that includes deflectable or flexible catheter body 410 and anchor balloon 415 mounted to a distal end of the catheter body 410. The inner catheter system 400a is movably disposed in the lumen 111 of outer catheter system 400b. The inner catheter system 400a protrudes beyond the distal end of the outer catheter system 400b when in use. The structures and features of the outer catheter system 400b, except the guide wire 112, are substantially the same as the catheter system 100.

The outer catheter system 400b includes multidirectional outer catheter body 110' that is French sizes and includes curls and flexion points to be multidirectional or deflectable. For example, the catheter body 110' may include a plurality of flexion points 103, 104 (shown in FIG. 2A) to facilitate the multidirectional deflections or bending. Unlike the catheter body 110 of the catheter system 100, the outer catheter body 110' of the catheter system 400b is configured to have channels 118 for fluid communication to outside of the catheter system 400. Anchor balloon 115 is mounted to the distal end of the catheter body 110'.

The flexile balloon tipped inner catheter system 400a includes a deflectable flexible inner catheter body 410 that includes a proximal end (not shown) and a distal end 402. The catheter body 410 is French sizes and flexible. The inner catheter body 410 has a length sufficient to reach a selected location in a patient's opposite extremity or other branch point in the venous or arterial system. The inner catheter body 410, together with the outer catheter body 110', is configured to be insertable into a femoral artery or vein or other vascular access as illustrated in FIG. 1A. The catheter body 410 includes a plurality of lumens. The plurality of lumens includes at least one main lumen 411 including an exit port 411a at the distal end 402, and a balloon lumen 414 for inflating and deflating at least one inner anchor balloon 415. The balloon lumen 414 includes a balloon control port (not shown) for connecting to a balloon control device accessible to an operator at the catheter proximal end and a balloon port 414a connected to the anchor balloon 415 near the multidirectional catheter distal end 402.

The plurality of lumens include one or more additional lumens 416 for delivery of drugs, pharmaceuticals, chemotherapeutics and embolization products to the selected locations or areas. The additional lumens 416 have exit ports 417 to discharge the pharmaceuticals into the selected locations or areas. As shown in FIG. 6A, the exit ports 417 are formed at longitudinal side surface of the inner catheter body 410 at proximal side from the anchor balloon 415. When the inner catheter system 400a advances by a predetermined distance L3, the exit ports 417 may be positioned between the two anchor balloons 115 and 415, and may be exposed to the outside of the catheter body 410. For illustration purpose, FIG. 6A exemplarily shows the additional lumens 416 and the exit ports 417 on the upper side of the catheter body 410 and FIG. 6B exemplarily shows four additional lumens 416. However, the number of the additional lumens is not limited to four. The additional lumens 416 have access ports at the proximal end of the catheter body 410, and external devices, such as drug delivery devices, may be connected to the access ports of the additional lumens 416.

Figure 7A:
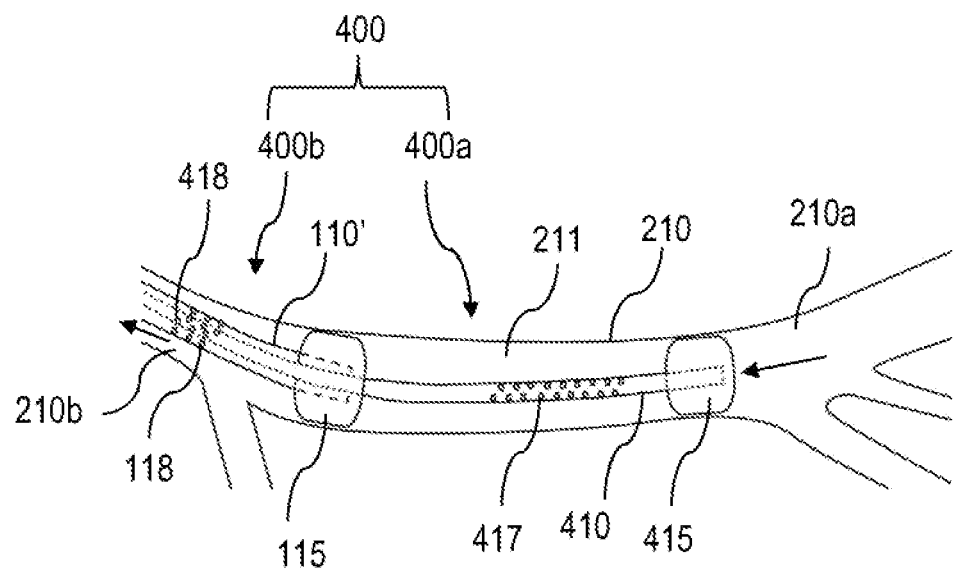
FIGS. 7A-7B show exemplary illustrations of single catheter system and dual catheter system conducting closed loop perfusion for treatment of DVT or other diseases in blood vessels.

As shown in FIGS. 6A-6B, the inner catheter body 410 has channels 418 that are formed at proximal side of the catheter body 410 from the anchor balloon 415 and are connected to the main lumen 411. The channels 418 form open fluid paths to the outside of the inner catheter body 410. The outer catheter body 110' has channels 118 that are configured to be substantially aligned with the channels 418 of the inner catheter body 410, when the inner catheter system 400a advances by a predetermined distance L3 from the distal end of the outer catheter system 400b. The channels 118 of the outer catheter body 110' form open fluid paths to the outside of outer the catheter body 110'. Consequently, the main lumen 411 of the inner catheter system 400a has open fluid paths to outside of the catheter system 400 through the channels 418 and 118. These channels 418 and 118 are formed at a proximal side form the anchor balloon 115 of the outer catheter body 110' as shown in FIG. 6A. Therefore, while the area between two anchor balloons 115 and 415 may be blocked and isolated, the area at the distal end 402 of the inner catheter system 400a may be open to the proximal outside area after the anchor balloon 115 through the lumen 411 and channels 418 and 118, as illustrated in FIG. 7A. FIGS. 6A-6B exemplarily show the channels 118, 418 at a bottom side of the catheter bodies, but the locations and numbers of the channels 118, 418 are not limited to these locations and numbers.

The multidirectional balloon tipped catheter systems 100 and 400 of the disclosed invention can be used in the venous system proximal and distal to the deep venous thrombosis (DVT). The anchor balloons are occlusive on the vein. This would allow for localized thrombolysis without any systemic complications from the thrombolytic. It may additionally also prevent pulmonary embolism (PE) because of embolization during catheter directed therapeutic procedures. It may allow for a more complete thrombectomy and therefore less PTS.

Figure 7B:
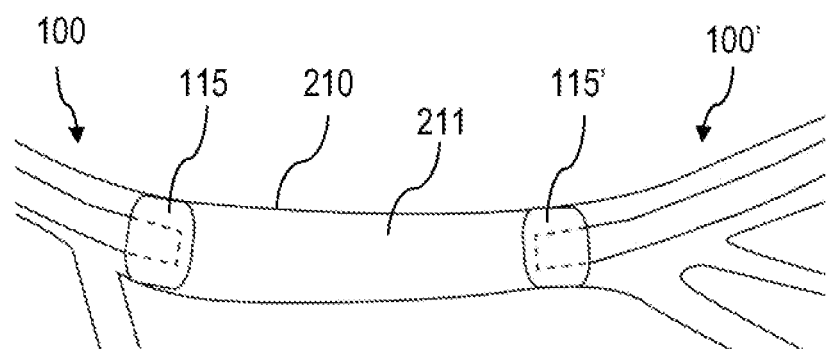

With reference to FIGS. 7A-7B, shown are exemplary illustrations which show multidirectional balloon tipped catheter systems 100, 400 for conducting closed loop perfusion for treatment of DVT or other diseases in blood vessels. For illustration purpose, FIGS. 7A-7B show vein 210 with area 211 that requires treatment such as removing blood clots. FIG. 7A shows the treatment procedure with the multidirectional balloon tipped catheter 400, which may be referred to as a single catheter system, and FIG. 7B shows the treatment procedure with two multidirectional balloon tipped catheters 100, 100', which is referred to as a dual catheter system. Referring to FIG. 7A, the catheter system 400 may be inserted into an entry point in a near femoral vein or other vascular access. For example, the catheter system 400 may be inserted through an entry point at left iliac/femoral vein (not shown) which is located opposite to the extremity (for example, right femoral vein 210). However, in the embodiment, the entry point is not limited to the opposite to extremity. The entry point may be in the extremity side. The catheter system 400 advances toward the area 211 that requires treatment. The anchor balloon 115 is inflated to anchor the outer catheter system 400b at a proper location (first location) near the treatment area 211, blocking blood flow through the first location. The inner catheter system 400a further advances passing the area 211 while the outer catheter 400b is anchored at the first location. At a proper location after passing the treatment area 211, the anchor balloon 415 is inflated to anchor the inner catheter system 400a at a second location. The inflated anchor balloon 415 blocks blood flow through the second location. With the anchor balloons 115, 415, the treatment area 211 is isolated for treatment. Blood flowing in the outer area 210a bypasses the treatment area 211 and flows into opposite outer area 210b through the open path formed by lumen 411 and channels 418 and 118. Pharmaceuticals are delivered to the treatment area 211 through the lumens 416 and the exit ports 417 connected to the lumens 416 of the inner catheter body 410.

In the dual catheter system shown in FIG. 7B, first catheter 100 may be inserted into an entry point in a near femoral vein or other vascular access, and advances toward the treatment area 211. The second catheter 100' is inserted into another entry point that is located at an opposite side of the treatment area 211, and advances toward the treatment area 211. The first catheter system 100 may be inserted in an entry point located opposite to the extremity while the second catheter system 100' may be inserted in an entry point at the extremity. The catheter systems 100, 100' are anchored at proper locations near the treatment area 211 by inflating anchor balloons 115, 115', respectively. The inflated balloons 115, 115' block blood flow through the anchored locations, and consequently, the treatment area 211 is isolated by the two anchor balloons 115, 115'. Pharmaceuticals are delivered to the treatment area 211 through one or more of the lumens 111, 125, 126 (shown in FIG. 3D) of the first catheter system 100 and/or the second catheter system 100'.

Figure 8A:
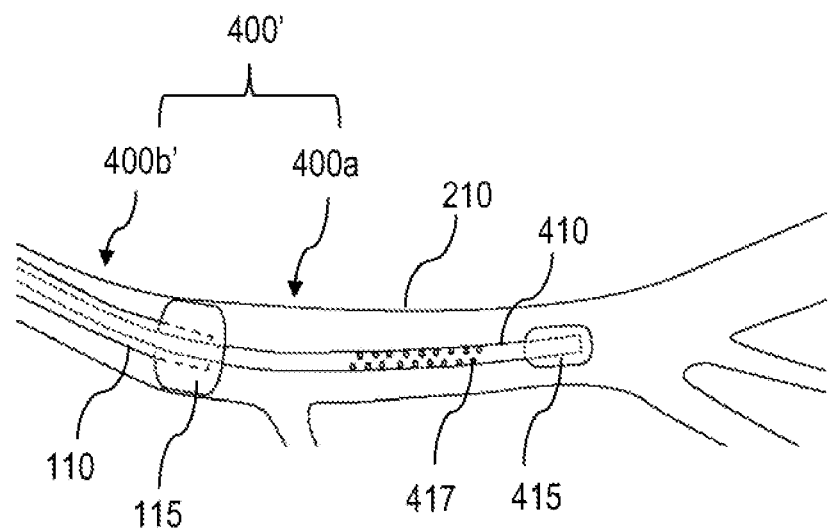
FIGS. 8A-8B show exemplary illustrations of single catheter system and dual catheter system conducting closed loop reperfusion for treatment of DVT or other diseases in blood vessels.
Figure 8B:
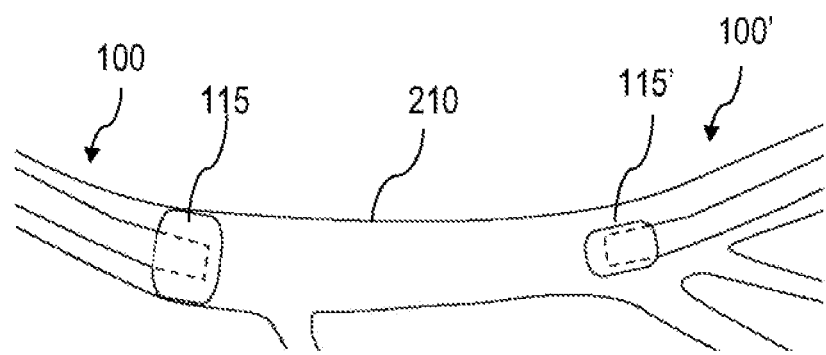

With reference to FIGS. 8A-8B, shown are exemplary illustrations which show multidirectional balloon tipped catheter systems 100, 400' for conducting closed loop reperfusion for treatment of DVT or other diseases in blood vessels. Referring to FIG. 8A, catheter system 400' is inserted into the vein 210. The outer catheter system 400b', which includes catheter body 110, is anchored at a location of the vein 210 by the inflated anchor balloon 115, blocking blood flow through the location. The inner catheter system 400a advances further to preform reperfusion. The balloon 415 of the inner catheter system 400a may not be fully inflated, allowing blood flow. Pharmaceuticals are delivered into the vein 210 through the lumens 416 and exit ports 417 formed on the catheter body 410. Referring to FIG. 8B, first catheter system 100 is inserted into the vein 210 through an entry point and second catheter system 100' is inserted into the vein 210 through another entry point. The first catheter system 100 is anchored at a location of the vein 210 by the inflated anchor balloon 115, blocking blood flow through the location. The second catheter system 100' is positioned at another location in the vein 210 to perform reperfusion. The balloon 115' of the second catheter system 100' may not be fully inflated, allowing blood flow. Pharmaceuticals are delivered into the vein 210 through the lumens 111 formed on the catheter body 110'.

Since many modifications, variations, and changes in detail can be made to the described preferred embodiments of the invention, it is intended that all matters in the foregoing description and shown in the accompanying drawings be interpreted as illustrative and not in a limiting sense. Consequently, the scope of the invention should be determined by the appended claims and their legal equivalents.

What is claimed is:

1. A multidirectional balloon tipped catheter system for conducting closed loop perfusion and reperfusion for treatment of deep venous thrombosis, comprising:
   a multidirectional catheter body having a proximal end and a distal end and including a plurality of curls and flexion points for multidirectional deflections, wherein the catheter body includes a plurality of lumens comprising:
      a main lumen including an exit port at the distal end; and
      at least one balloon lumen including a balloon port near the distal end;
   an anchor balloon mounted to near the distal end of the catheter body, wherein the anchor balloon is in fluid communication with the balloon port and wherein the anchor balloon overhangs the distal end of the catheter body by a predetermined distance when the anchor balloon is inflated; and
   an inner catheter device disposed in the main lumen, wherein the inner catheter device comprises:
      a flexible inner catheter body including a center lumen, at least one balloon lumen, and a plurality of additional lumens, wherein the inner catheter body is configured to advance beyond the distal end of the multidirectional catheter body, and wherein the additional lumens include exit ports open to outside of the inner catheter body; and
      an anchor balloon mounted to near the distal end of the inner catheter body, wherein the anchor balloon is in fluid communication with the balloon lumen and wherein the anchor balloon overhangs the distal end of the inner catheter body by a predetermined distance when the anchor balloon is inflated.

2. The multidirectional balloon tipped catheter system of claim 1 wherein the anchor balloon and the anchor balloon of the inner catheter device are inflated with a fluid including air, saline, or contrast, and are configured to be inflated in various sizes.

3. The multidirectional balloon tipped catheter system of claim 1 wherein the exit ports of the additional lumens of the inner catheter device are formed at proximal side from the anchor balloon of the inner catheter device.

4. The multidirectional balloon tipped catheter system of claim 1 wherein:
   the multidirectional catheter body includes channels that are connected to the main lumen and are open to outside of the multidirectional catheter body;
   the inner catheter body includes channels that are connected to the center lumen and are open to outside of the inner catheter body; and
   the channels of the multidirectional catheter body are configured to be substantially aligned with the channels of the inner catheter body to form open fluid paths, when the inner catheter device advances by a predetermined distance.

5. The multidirectional balloon tipped catheter system of claim 4 wherein the exit ports of the additional lumens of the inner catheter device are configured to be exposed outside the main lumen for delivery of pharmaceuticals, chemotherapeutics and embolization products to a selected location, when the inner catheter device advances by the predetermined distance.

6. The multidirectional balloon tipped catheter system of claim 1 wherein the multidirectional catheter body is configured to be insertable into a femoral vein or other vascular access.

7. The multidirectional balloon tipped catheter system of claim 1 wherein the anchor balloon overhangs the distal end of the catheter body by at least two millimeters when the anchor balloon is inflated.

8. The multidirectional balloon tipped catheter system of claim 1 wherein a diameter of the anchor balloon is configured to occlude a vascular channel at a selected location.

9. The multidirectional balloon tipped catheter system of claim 1 wherein the catheter body is configured to be insertable into a femoral artery or other vascular access.

* * * * *